(12) United States Patent
Billard

(10) Patent No.: US 12,727,824 B2
(45) Date of Patent: Sep. 8, 2026

(54) PERINEAL PROBE

(71) Applicant: APPAREILS POUR KINES SPORTS ET ESTHETIQUE, Pérols (FR)

(72) Inventor: Georges Robert Billard, Perols (FR)

(73) Assignee: APPAREILS POUR KINES SPORTS ET ESTHETIQUE, Pérols (FR)

( * ) Notice: Subject to any disclaimer, the term of this patent is extended or adjusted under 35 U.S.C. 154(b) by 316 days.

(21) Appl. No.: 18/697,109

(22) PCT Filed: Sep. 29, 2022

(86) PCT No.: PCT/EP2022/077232
§ 371 (c)(1),
(2) Date: Mar. 29, 2024

(87) PCT Pub. No.: WO2023/052567
PCT Pub. Date: Apr. 6, 2023

(65) Prior Publication Data

US 2024/0407727 A1 Dec. 12, 2024

(30) Foreign Application Priority Data

Sep. 30, 2021 (FR) ...................................... 2110352

(51) Int. Cl.
*A61B 5/00* (2006.01)
*A61B 5/22* (2006.01)
(Continued)

(52) U.S. Cl.
CPC ............ *A61B 5/6847* (2013.01); *A61B 5/227* (2013.01); *A61B 5/251* (2021.01); *A61B 5/296* (2021.01);
(Continued)

(58) Field of Classification Search
CPC ......... A61B 5/227; A61B 5/251; A61B 5/296; A61B 5/391; A61B 5/43; A61B 5/4337;
(Continued)

(56) References Cited

U.S. PATENT DOCUMENTS

2006/0064038 A1* 3/2006 Omata .................. A61B 5/103
600/587
2009/0281397 A1 11/2009 Pibrre
(Continued)

FOREIGN PATENT DOCUMENTS

| | | |
|---|---|---|
| CN | 113274028 | 8/2021 |
| FR | 2827520 | 1/2003 |
| WO | 2016202697 | 12/2016 |

OTHER PUBLICATIONS

International Search Report dated Jan. 18, 2023.

*Primary Examiner* — Eun Hwa Kim
(74) *Attorney, Agent, or Firm* — IPSILON USA, LLP

(57) ABSTRACT

A perineal probe (10) having a probe body which includes electronic members (110, 111, 112) configured to interact with perineal muscles of the patient. The probe body has a cylindrical portion (12) configured to be positioned at the opening of the body cavity of a patient, and a flared portion (13) which extends from one end (121) of the cylindrical portion (12). The flared portion (13) extends widening from the cylindrical portion (12) as far as a free upper end (130), with the flared portion (13) being elastically deformable between a retracted position and a deployed position. The electronic members (110, 111, 112) are arranged on the flared portion (13) and/or on the cylindrical portion (12).

14 Claims, 8 Drawing Sheets

(51) Int. Cl.

| | |
|---|---|
| ***A61B 5/251*** | (2021.01) |
| ***A61B 5/296*** | (2021.01) |
| ***A61B 5/391*** | (2021.01) |
| ***A61B 90/00*** | (2016.01) |
| ***A61N 1/36*** | (2006.01) |

(52) U.S. Cl.
CPC ............ *A61B 5/391* (2021.01); *A61B 5/4337* (2013.01); *A61B 90/06* (2016.02); *A61B 2090/064* (2016.02); *A61B 2560/0406* (2013.01); *A61B 2560/0468* (2013.01)

(58) Field of Classification Search
CPC ................ A61B 5/6847; A61B 5/6867; A61B 2018/00517; A61B 2018/00523; A61B 2018/00559; A61N 1/0512; A61N 1/0524; A61N 1/36007; A61H 19/44
See application file for complete search history.

(56) References Cited

U.S. PATENT DOCUMENTS

| | | | |
|---|---|---|---|
| 2013/0018281 A1 | 1/2013 | Nagale et al. | |
| 2018/0055563 A1 | 3/2018 | Shetake et al. | |
| 2019/0160332 A1 | 5/2019 | Beer et al. | |
| 2021/0015551 A1* | 1/2021 | Fuentes-Ortega | A61B 18/1492 |

* cited by examiner 14b
145
140
141
144
d

142
ρ
143
H
145
14a
141
142
ρ
144
d

H
143
140

PERINEAL PROBE

RELATED APPLICATION

This application is a National Phase of PCT/EP2022/077232 filed on Sep. 29, 2022, which claims the benefit of priority from French Patent Application No. 21 10352 filed on Sep. 30, 2021, the entirety of which are incorporated by reference.

TECHNICAL FIELD

The invention concerns a perineal probe and more particularly a probe for the diagnosis and rehabilitation of the perineum. On a broader scale, the invention lies in the paramedical and medical fields, and aims in particular to analyze the functional status of anatomical structures involved in the mechanism of urinary and/or fecal continence and/or incontinence.

Continence is a complex mechanism that implies an acquired anticipation reflex and an innate myotatic reflex which in response to a stimulus acts on a plurality of groups of muscles. The stimulus generally corresponds to an increase in the intra-abdominal pressure. In response to this stimulus the anticipation reflex and the myotatic reflex drive the contraction of groups of muscles with a view to preventing urinary and/or fecal leakage.

Thus a first group of muscles comprises the urethral and anal sphincters that respectively surround the urethra and the anal passage. Because of the effect of their respective contraction the urethra and the anal passage close. The muscles of the perineum constitute a second group of muscles that participate in the continence mechanism. The perineum is a set of muscles that extend from the pubis to the coccyx. The perineum generally exerts two functions: on the one hand, it retains the abdominal content: rectum, bladder, uterus, and, on the other hand, it participates in damping abdominal hyperpressure and in closure of the bladder and the rectum. In fact, the perineum is known to play an important role in the continence mechanism.

With regard to these physiological functions, medical practitioners and industry are interested in the perineum for diagnosing and treating incontinence problems in male patients and in female patients.

PRIOR ART

From the point of view of medical practitioners, the first method of assessing the functional status of the perineum, which is still in use at present, is a manual method that involves palpation of the vagina or the rectum. During this medical procedure the medical practitioner evaluates the contraction initiated by the patient. In accordance with this method the assessment of the functional status of the perineum is performed in accordance with subjective criteria that correlate strongly with the personal experience of the medical practitioner. In this context neither diagnosis nor functional rehabilitation guarantee any regularity in the assessment of dysfunction and the result of rehabilitation.

There are already known perineal probes for the functional analysis and rehabilitation of the anatomical structures involved in the mechanism of continence or incontinence.

Most known prior art perineal probes include a probe body of cylindrical shape that has a rounded free end. The probe body includes two annular electrodes disposed at a particular distance from one another. This type of perineal probe is designed to be introduced into the vaginal cavity of a patient and/or the anal cavity of a patient. Depending on their dimensions, this kind of probe can cause discomfort during insertion and withdrawal of the probe from the vaginal or anal endocavity. Furthermore, this type of probe is generally designed for the rehabilitation by electrotherapy of the connecting tissue that surrounds the vagina and/or the anal cavity and also the muscles surrounding the vaginal or anal cavity. However, the annular character of the electrodes does not allow isolation of the muscles from one another in order to target the diagnosis or the electrotherapy. Moreover, the cylindrical shape of the body of the probe does not allow this type of probe to be retained in position during examination or the rehabilitation protocol. In fact, this type of probe tends to exit the endocavity if the intra-abdominal pressure increases, which renders examination or rehabilitation time-consuming. In this context it is difficult to determine the functional status of the muscles that surround the endocavity in an orthostatic or orthodynamic situation of the everyday life of the patient that is liable to cause urinary or fecal leakage.

The document FR 2 941 860 describes another example of a perineal probe that is designed to be inserted in the vaginal cavity. This type of probe enables measurement of the tone of the connecting tissue that surrounds the vaginal cavity. This perineal probe includes two articulated and complementary branches. At least one branch has a curved end that comes to cover the free end of the other branch in order to form a rounded probe head. Each branch carries a force sensor in order to determine the pendular movement of the branches from a force difference measured between front and rear sensors. After inserting the probe into the vaginal cavity the medical practitioner separates the branches disposed along an anterior-posterior axis. If a small reduction of force on the front sensor is measured, the connecting tissue is of good quality and follows the movement of the branches. Conversely, if a large reduction of the force is measured the connecting tissue is of poor quality and follows more slowly the movement of the branches of the probe. Poor connecting tissue quality is a known factor in incontinence. If the medical practitioner obtains such a diagnosis, they can apply electrostimulation techniques that improve the trophic level and the tone of the connecting tissues.

This type of probe is not comfortable for patients and must be held in position by the medical practitioner during the examination. Furthermore, this type of probe does not enable differentiated determination of the dysfunction of the anatomical structures involved in the mechanism of locking the urethra or the anal passage.

The invention aims to address the disadvantages of the prior art.

STATEMENT OF INVENTION

The invention aims in particular to provide a perineal probe limiting discomfort both during its insertion into the vaginal or anal endocavity of the patient as during its use and during the withdrawal of the perineal probe.

The invention also aims to provide an endocavity perineal probe that is held in position in the vaginal or anal endocavity in use. In particular, the invention aims to provide an endocavity perineal probe that remains in position while the patient remains standing to effect physical movements that are liable to cause urinary or fecal leakage.

The invention also aims to provide a diagnostic and/or rehabilitation tool capable of evaluating the functional status and/or treating in a differentiated and dissymmetrical manner the deep layers and the superficial layers of the perineum.

Embodiments of the invention aim to propose a perineal probe that is able to adapt to the anatomical dimensions of a great many patients.

In this framework, the invention concerns a perineal probe comprising a probe body which includes:

- a cylindrical portion configured to be positioned at the opening of the vaginal or anal endocavity of a patient,
- a flared portion which extends from one end of the cylindrical portion, the flared portion extends in a flared manner from the cylindrical portion to a free upper end, the flared portion being elastically deformable between a folded position and a deployed position so as to rest on the walls of the endocavity, and
- electronic organs configured to interact with the muscles of the perineum of a patient, the electronic organs being disposed on the flared portion and/or on the cylindrical portion.

The perineal probe in accordance with the invention is characterized in that the flared portion includes, on the one hand, at least one lateral wall which has an internal face delimiting a conical internal volume of the flared portion, and, on the other hand, the flared portion includes at least one longitudinal groove which extends in a plane of symmetry of the perineal probe.

The conformation of the body of the perineal probe which has a cylindrical bottom part and a flared top part enables the perineal probe to remain in position when the patient performs exercises or movements in which their urinary or fecal leaks occur in everyday life. Furthermore, the deformable character of the flared portion makes it possible to reduce the discomfort linked to insertion of the probe into the endocavity but also to press the flared portion against the walls of the endocavity once the perineal probe is in position in said endocavity. The vaginal or anal endocavity is naturally collapsed and after its insertion into the endocavity the flared portion is deployed and comes to bear against the walls of the endocavity, which walls are therefore collapsed against the underlying perineal muscles. Furthermore, the disposition of the electronic members on the bottom part and/or on the top part of the body of the probe enables targeting of the muscles of the deep layers and/or the superficial layers of the perineum. The hollow character of the flared portion and the longitudinal groove improve the amplitude of deformation of the flared portion.

In embodiments of the invention the longitudinal groove extends in a median sagittal plane of symmetry of the perineal probe and divides said at least one lateral wall into two half-walls.

In embodiments of the invention the flared portion includes at least one groove that extends transversely relative to the median sagittal plane PSM of the perineal probe, said groove extending on the exterior face of the lateral wall at the level of a base disposed at the junction between the flared portion and the cylindrical portion. Said groove reduces the thickness of the lateral wall at the level of its base in order to increase the amplitude of folding of the flared portion.

In embodiments of the invention the flared portion may include at least one opening disposed in a plane of symmetry of the perineal probe. The opening also improves the amplitude of deformation of the probe. To be more precise, the flared portion may include:

- a lateral opening disposed in a plane of symmetry of the perineal probe, and
- a top opening disposed at the level of the free upper end of the flared portion.

In embodiments of the invention the perineal probe may include a retaining member that is mobile between a deployed position and a folded position and in which, in the deployed position, the retaining member enables the flared portion to be retained in position in the endocavity of the patient and, in the folded position, the retaining member enables insertion of the perineal probe into the endocavity. The lateral and top openings in the flared portion improve the folding of the retaining member that in the folded position is disposed in the internal volume of the flared portion. This confers greater compactness on the head of the perineal probe for its insertion into the endocavity.

To be more precise the retaining member may include a tongue that projects from the flared portion toward a free end, the tongue projecting in a plane of symmetry of the perineal probe. Thus the tongue can exert an elastic force against the wall of the endocavity. The elastic force then participates in retaining the perineal probe in the endocavity. In particular, the tongue exerts pressure on the anterior wall of the vagina or of the rectum in such a manner as to press that wall against the deep perineal muscles. In a complementary manner the tongue may have a striated surface at its free end. This striated surface is then able to cooperate with the wall of the endocavity which in the case of the vagina also includes striations.

Furthermore, the retaining member may be attached to the cylindrical portion in a detachable manner. This makes it possible to provide a plurality of sizes of tongues in order to adapt to the anatomy of the patient. Furthermore, in the deployed position the tongue may project from the flared portion along an anterior-posterior axis situated in the plane. In accordance with this disposition the tongue in the deployed position exerts an anterior-posterior force on the wall of the vaginal or anal endocavity that contributes to retaining the perineal probe in position, in particular if the patient performs positional physical exercises for evaluating the functional status of the muscles of the perineum.

In embodiments of the invention the flared portion may extend at an angle of inclination $\alpha$ relative to a lateral wall of the cylindrical portion, the angle of inclination $\alpha$ being between 7° and 40° inclusive. The inclination of the flared portion corresponds to the natural anterior-posterior inclination of the vagina. This inclination improves the retention of the perineal probe in the endocavity but also serves as a polarizer and the perineal probe can then be inserted into the endocavity in only one anterior-posterior orientation.

In embodiments of the invention the flared portion includes two electronic members disposed on either side of a plane of symmetry of the perineal probe. This enables differentiated interaction with the muscles of the deep layer of the perineum that are situated on either side of the endocavity.

In embodiments of the invention the cylindrical portion may include electronic members disposed on either side of a plane of symmetry of the perineal probe. This enables differentiated interaction with the muscles of the superficial layer of the perineum that are situated on either side of the endocavity.

To be more precise, the cylindrical portion and the flared portion may include respective electronic members consisting of EMG electrodes, the electronic members being disposed on either side of a median sagittal plane PSM of the perineal probe. Thus it is possible to measure the electromyographic activity of the muscles of the superficial and deep layers of the perineum in a differentiated manner on either side of the endocavity.

In embodiments of the invention the electronic members disposed in an anterior-posterior manner on either side of a median transverse plane PTM of the perineal probe include two force sensors. It is therefore possible to measure in an isolated manner the anterior-posterior forces that are applied at the lower end of the endocavity.

DESCRIPTION OF THE DRAWINGS

Other features and advantages of the invention will become more clearly apparent on reading the following description. The latter is purely illustrative and must be read with reference to the appended drawings, in which.

DESCRIPTION OF EMBODIMENTS

The present invention concerns a perineal probe 10. This perineal probe is designed for diagnosis and rehabilitation of the perineum of a patient. The perineal probe 10 in accordance with the invention is configured to be at least partly inserted into the vaginal cavity of a patient. However, the perineal probe 10 may equally be inserted into the anal cavity of a patient. This makes it possible in particular to treat male patients suffering from fecal incontinence. In the present document the term endocavity designates interchangeably the vaginal cavity and the anal cavity of a patient.

Referring to FIGS. 1 to 6, the perineal probe 10 includes a probe body that includes electronic members 110, 111, 112 configured to interact via the walls of the endocavity with the muscles of the perineum of a patient.

Figure 4:
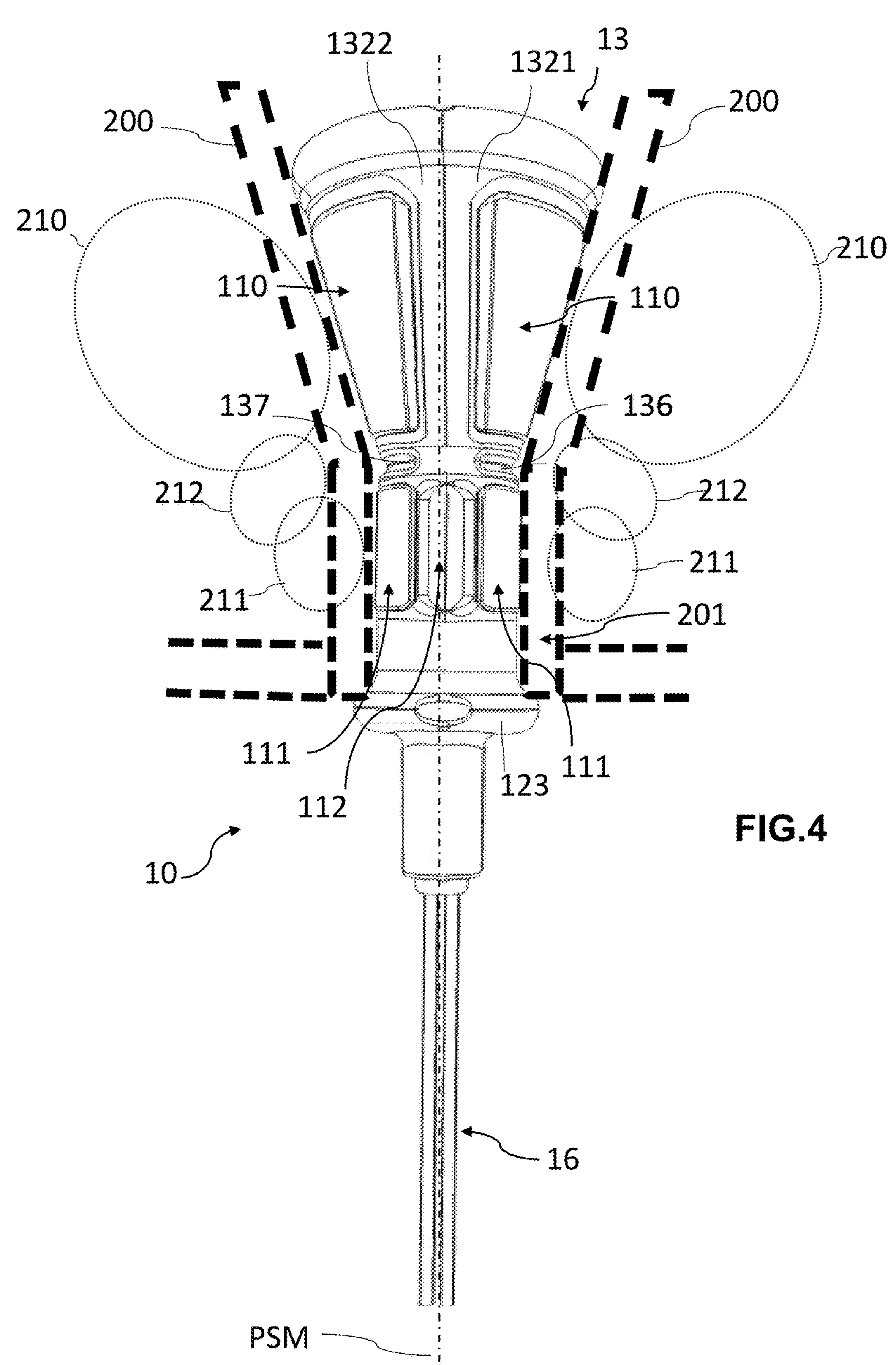
FIG. 4 is a representation as seen from the rear of the perineal probe in FIG. 1, the perineal probe being, diagrammatically, situated in an endocavity of a patient.

As depicted in FIG. 4, the probe body includes a cylindrical portion 12 configured to be positioned at the level of the lower end 201 of the endocavity of a patient. In this example the probe body is made of a medical polymer material such as silicone or polyurethane. In particular, the selected polymer material has elasticity and sealing properties.

As depicted in FIGS. 1 to 6, the cylindrical portion 12 has a first end 120 and a second end 121 that are opposite one another. Here the first end 120 of the cylindrical portion 12 is a free end. In the present document the first end 120 defines the lower end of the perineal probe 10. By convention the terms “bottom” and “lower” and derivatives thereof, when used specifically with reference to the perineal probe 10, designate the first longitudinal end 120 of the cylindrical portion 12.

The second end 121 of the cylindrical portion 12 has an upper wall 124 that delimits the upper end of the cylindrical portion 12.

In this example the cylindrical portion 12 comprises a first section and a second section. The cylindrical portion 12 may be equipped with an annular bead 123. Here the annular bead 123 is disposed at the junction between the first section and the second section of the cylindrical portion 12. The annular bead 123 espouses the anatomy of the patient at the opening of the endocavity. For example, for a female subject, when the perineal probe 10 is inserted into the vaginal cavity, the annular bead 123 is placed in contact with the labia minora of the vulva of the patient. Thus the first section extends longitudinally between the annular bead 123 and the second end 121 of the cylindrical port 12 (depicted in FIG. 4).

As depicted in FIGS. 1 and 3 to 6, the first section is able to support electronic members 111, 112. At the level of the first section the cylindrical portion 12 is delimited by a lateral wall 122. Furthermore, the second section of the cylindrical portion 12 extends from the annular bead 123 to the first end 120 of the cylindrical portion 12. The second portion has dimensions smaller than the dimensions of the first section.

The body of the perineal probe 10 also includes a flared portion 13 that extends from one end 121 of the cylindrical portion 12 to the free upper end 130. In the present document the free upper end 130 of the flared portion 13 defines an upper longitudinal end of the perineal probe 10. By convention, the terms “top” and “upper” and derivatives thereof, when used specifically with reference to the perineal probe 10, designate the free end 130 of the flared portion. The body of the perineal probe 10 can measure between 5 cm and 15 cm between its bottom end and its upper end.

Figure 3:
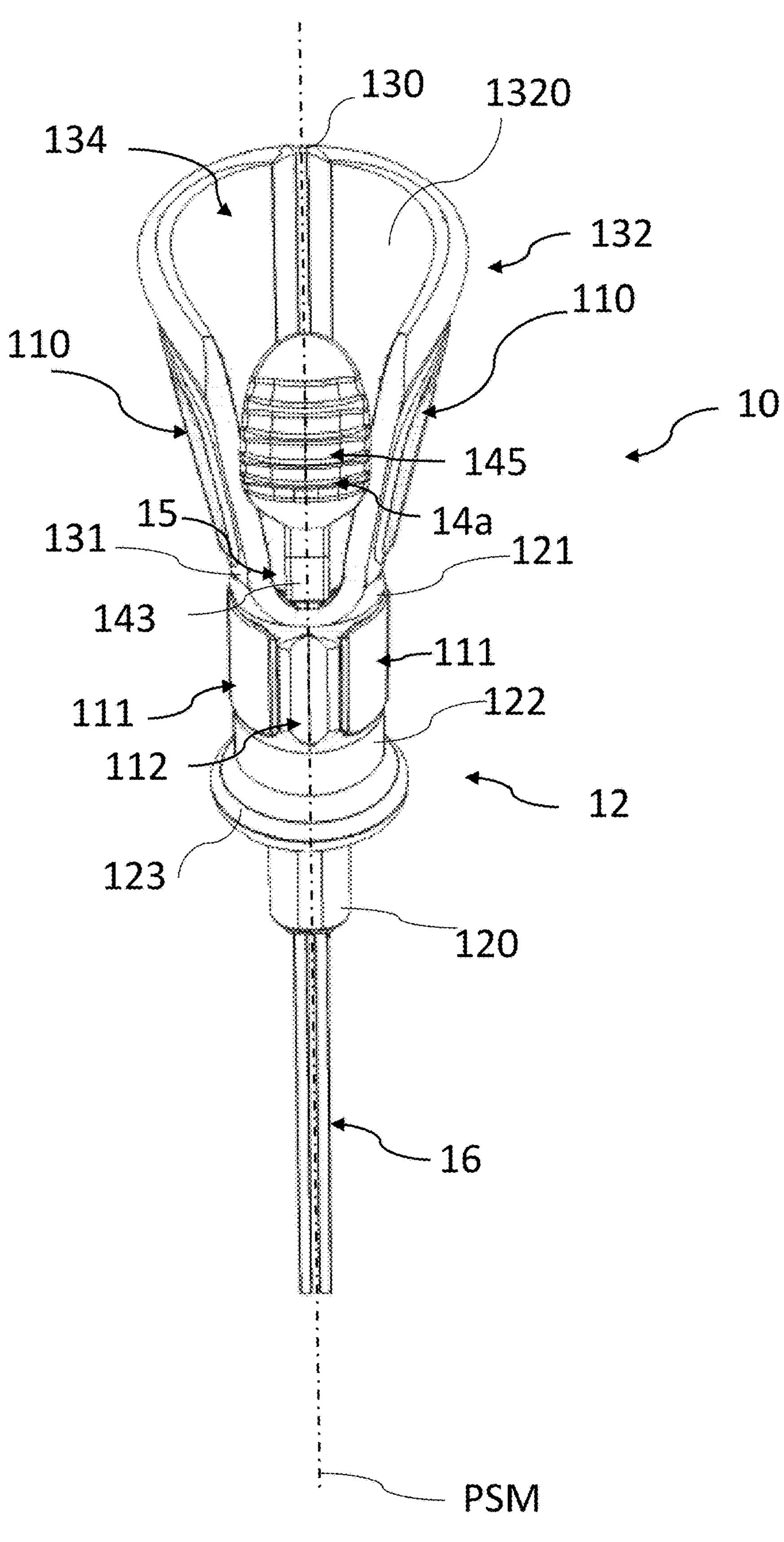
FIG. 3 is a representation in perspective as seen from the front of the perineal probe in FIG. 1.
Figure 6:
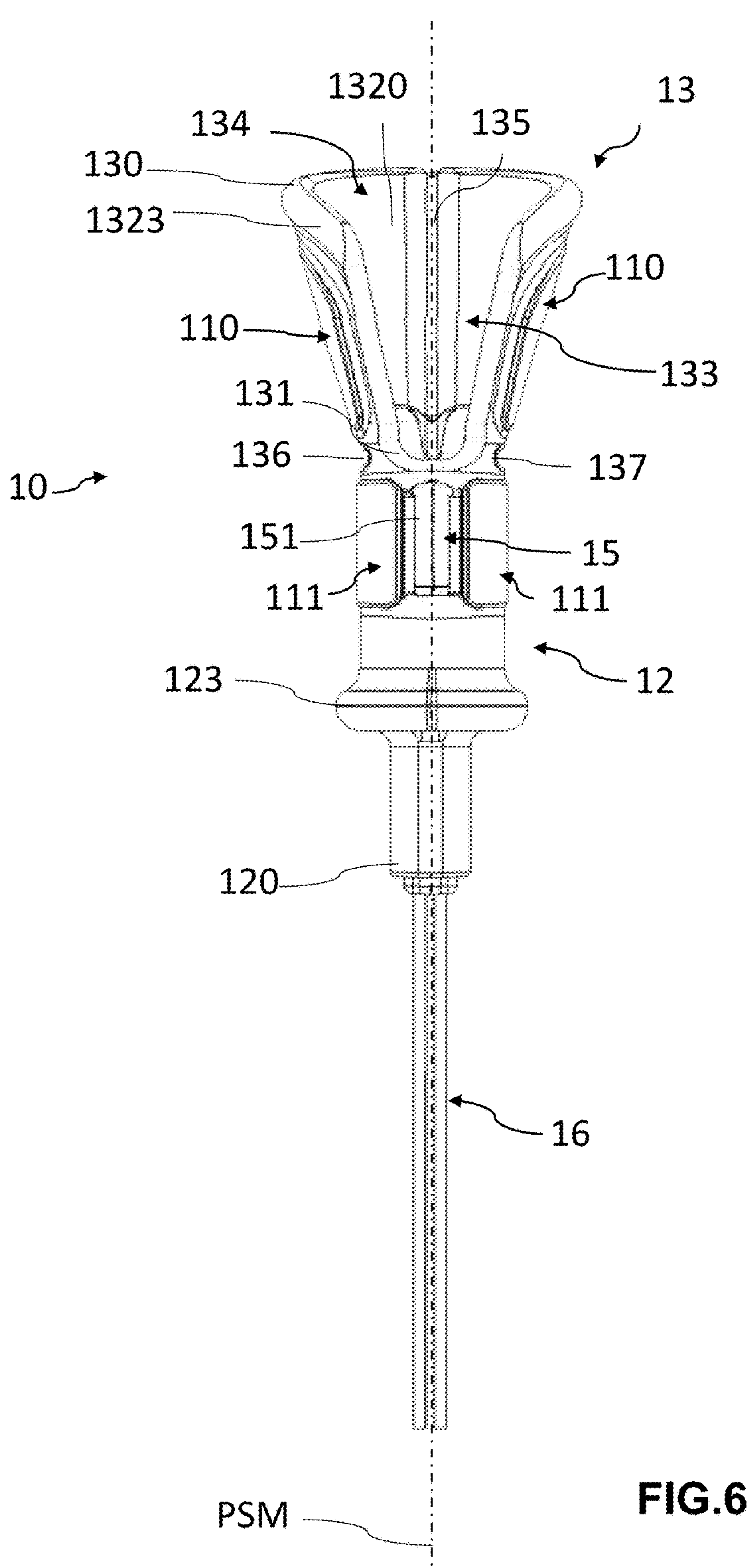
FIG. 6 is a representation as seen from the front of one embodiment of the perineal probe in accordance with the invention, the perineal probe including means for receiving the tongue on the lateral wall of the cylindrical portion of the perineal probe.

As depicted in FIGS. 3, 4 and 6, the flared portion 13 extends in flared manner from the cylindrical portion 12 to a free upper end 130 of the flared portion 13. In particular, the flared portion 13 includes a base 131 disposed at the junction with the second end 121 of the cylindrical portion 12 of the probe body. In the present example the flared portion 13 extends from the base 131 to the free upper end 130 of the flared portion 13. To be more precise, the base 131 of the endocavity body 13 is secured to the upper face 124 of the cylindrical portion 12. The flared portion 13 constitutes the head of the perineal probe 10.

Furthermore, the flared portion 13 is elastically deformable between a folded position and a deployed position. In the folded position the head of the perineal probe 10 occupies a small volume that facilitates the insertion of the perineal probe 10 into the endocavity. This improves the comfort of the patient. Furthermore, in the deployed position the head of the probe is able to bear on the walls of the endocavity. Because of this the perineal probe 10 is retained in the endocavity of a patient by the flared portion 13 in the deployed position. The vaginal or anal endocavity being naturally collapsed at rest, applying pressure to the walls of the endocavity enables those walls to be brought into contact with the anatomical structures surrounding the endocavity such as the muscles of the perineum.

In particular, as depicted in FIGS. 1 to 6 the flared portion 13 includes at least one lateral wall 132. Here the lateral wall 132 extends in flared manner from the base 131 toward the free upper end 130 of the flared portion 13. The lateral wall 132 has an internal face 1320 that delimits a conical internal volume of the flared portion 13 (depicted in FIG. 2).

In the present example the flared portion 13 includes at least one opening 133, 134 disposed in a plane of symmetry of the perineal probe 10. The opening or openings facilitate (s) the elastic deformation of the flared portion 13 for more comfortable insertion of the probe into the endocavity. In particular, the flared portion 13 includes a lateral opening 133 and a top opening 134.

The lateral opening 133 is disposed in a plane of symmetry of the perineal probe 10. As depicted in FIG. 6, the lateral opening 133 extends longitudinally on either side of a median sagittal plane PSM of the perineal probe 10. The median sagittal plane represented in FIGS. 1 to 4 and 6 defines a longitudinal plane of symmetry in accordance with a sagittal orientation of the perineal probe 10. The lateral opening 133 extends from the base 131 of the head as far as the free upper end 130 of the perineal probe 10. As depicted in FIG. 6, the lateral opening 133 has a U-shape that extends from the base 131, the branches of the U diverging from one another as far as the upper end 130 in such a manner as to form a flared lateral opening 133.

Figure 2:
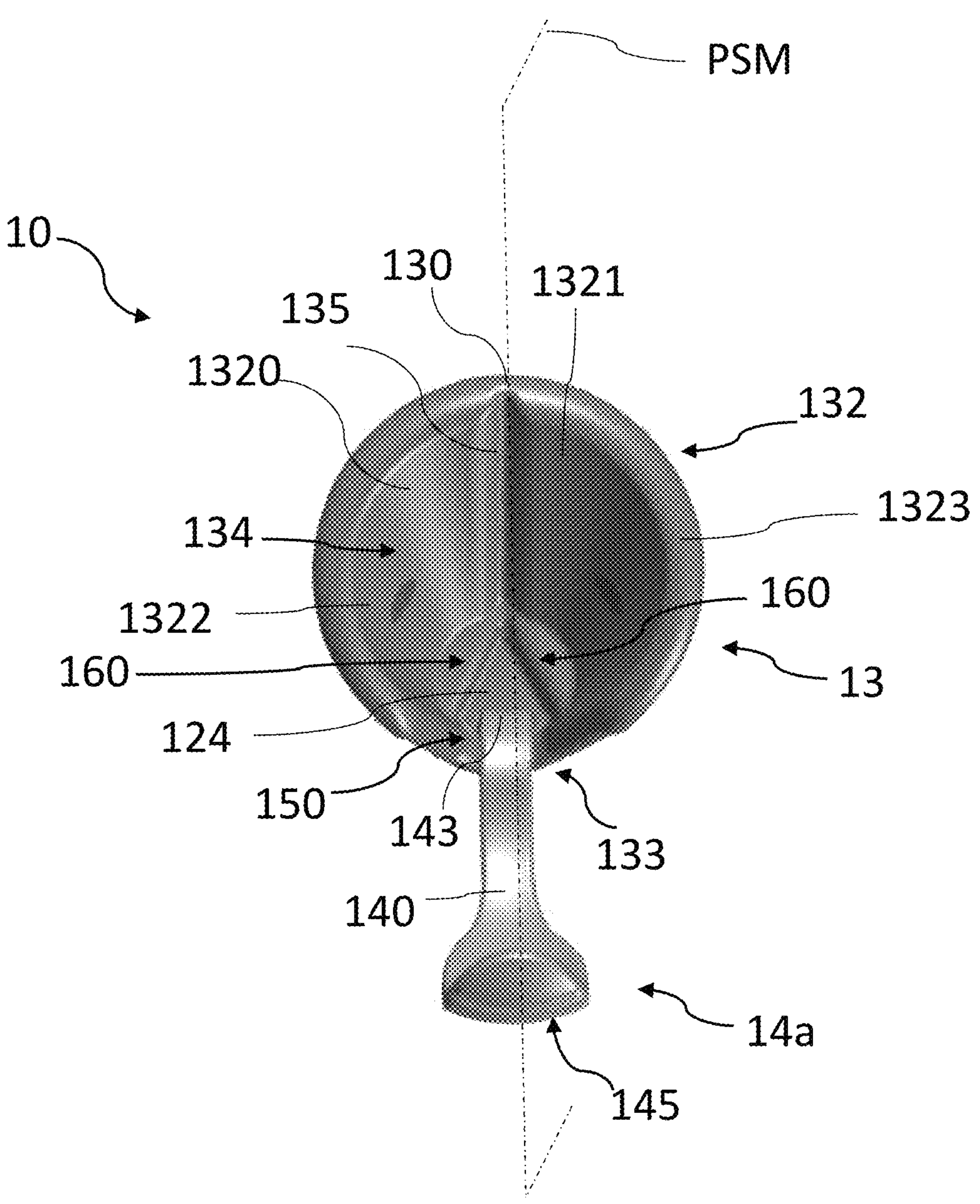
FIG. 2 is a representation as seen from above of the flared portion of the perineal probe in FIG. 1.

As depicted in FIGS. 2, 3 and 6 in particular, the top opening 134 is disposed at the level of the free upper end 130 of the flared portion 13. As depicted in FIG. 2, the top opening 134 is symmetrical with respect to the median sagittal plane PSM of the perineal probe 10. The lateral opening 133 includes a top bead 1323 that delimits at least partially the top opening 134. The top bead 1323 contributes to the comfort of the patient during insertion of the perineal probe 10 into the endocavity.

Figures 7, 8:
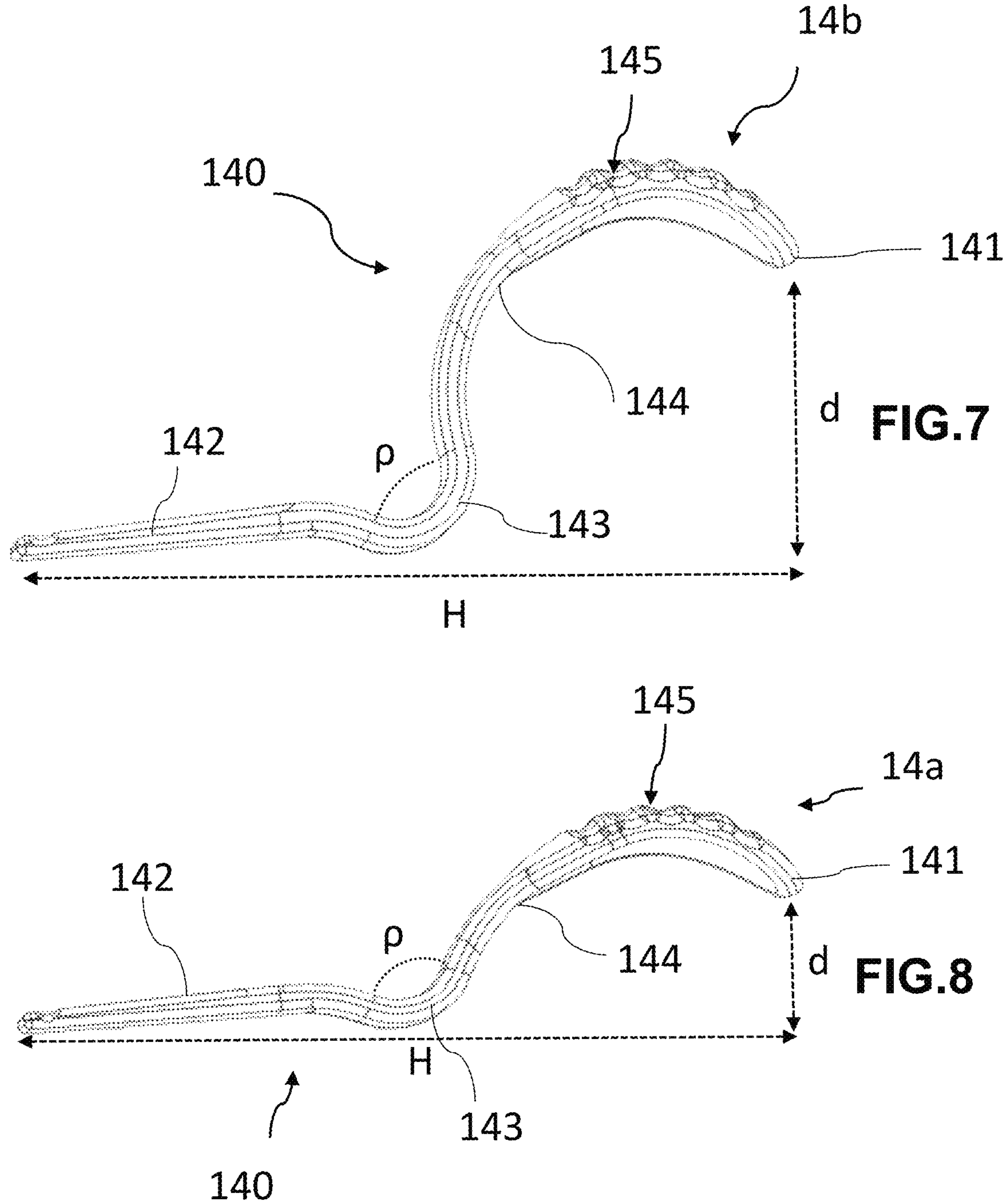
FIG. 7 and [FIG. 8] are representations as seen from the side of two retaining members of different size of the perineal probe in FIG. 1.

As depicted in FIG. 7, the top opening 134 extends in a plane intersecting the lateral opening 133, the two openings 133, 134 being disposed in continuity with one another along a median sagittal axis of the perineal probe 10. Here the median sagittal axis is disposed in the median sagittal plane PSM of the perineal probe 10.

As depicted in FIGS. 1 to 4 and 6, the flared portion 13 includes at least one groove 135, 136, 137. Each groove 135, 136, 137 increases the amplitude of the elastic deformation of the flared portion 13.

In particular, the flared portion 13 includes a longitudinal groove 135 that extends in the median sagittal plane PSM. Here the longitudinal groove 135 divides the flared portion 13 into two half-walls 1321, 1322 in the median sagittal plane PSM of the perineal probe 10. In practise, the groove 135 extends at least partly between the base 131 and the free upper end 130 of the flared portion 13. In the example depicted in FIG. 2 the groove 135 extends the full height of the flared portion 13 between the base 131 and the free upper end 130.

As depicted in FIG. 2, the two half-walls 1321, 1322 are curved so as to form a corolla. In particular, the half-walls 1321, 1322 are curved in a convex manner relative to the median sagittal plane PSM.

The medical practitioner can then move the flared portion 13 from its deployed position to the folded position by pinching the half-walls 1321, 1322 in order to fold the head of the perineal probe 10 in the median sagittal plane PSM. The longitudinal groove 135 advantageously makes it possible to increase the amplitude of the folding of the head of the perineal probe 10.

Figure 1:
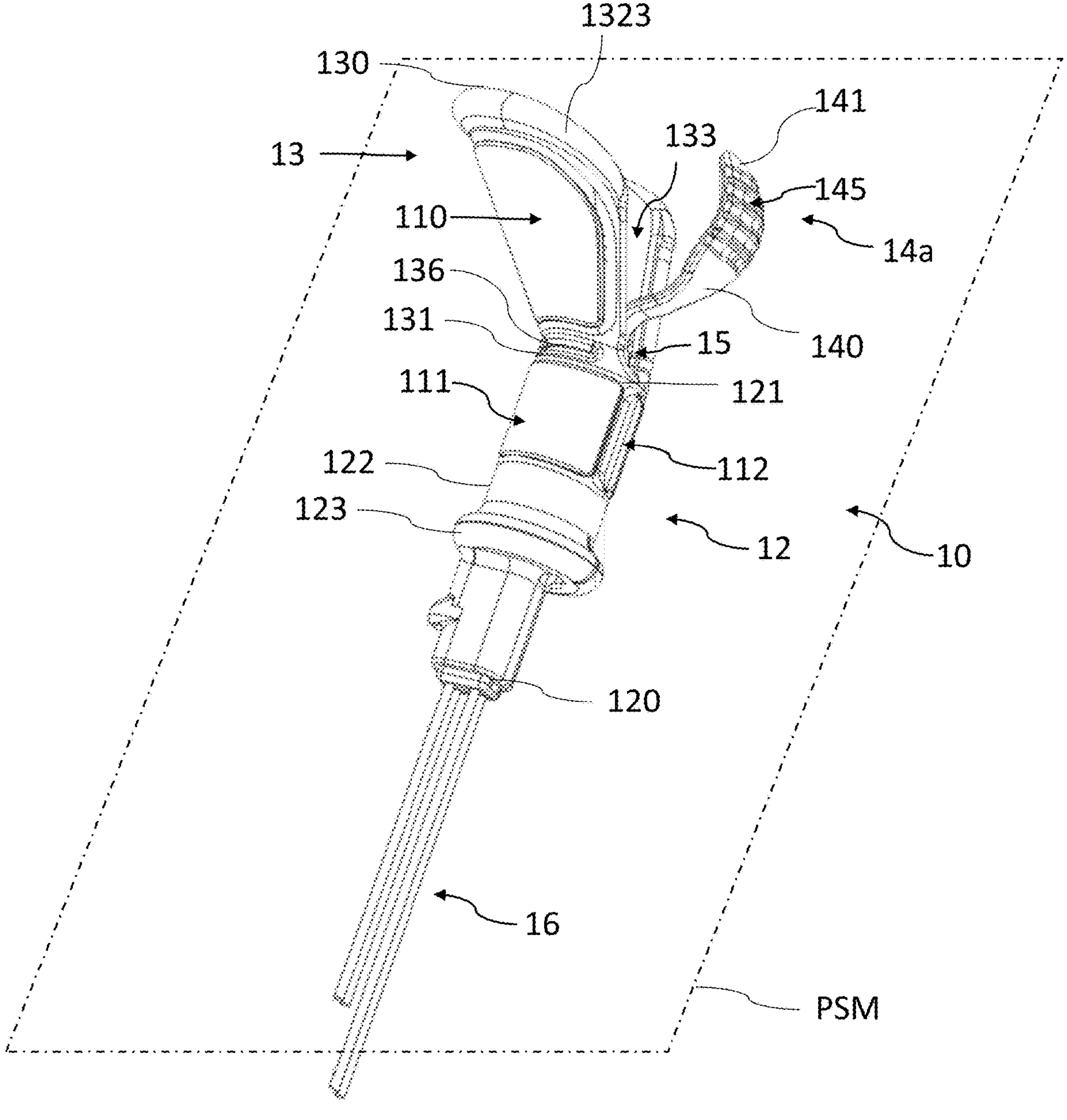
FIG. 1 is a representation in perspective of a perineal probe in accordance with the invention.

In the example in FIGS. 1, 4 and 6 the flared portion 13 includes at least one groove 136, 137 that extends at the level of the base 131 on the exterior face of the lateral wall 132. The groove or grooves 136, 137 extend(s) transversely relative to the median sagittal plane PSM over at least a part of the circumference of the base 131 of the flared portion 13. These grooves 136, 137 reduce the thickness of the lateral wall 132 in order to increase the amplitude of folding of the flared portion 13. In this example the flared portion 13 includes two transverse grooves 136, 137 that are symmetrical relative to the median sagittal plane PSM. The two transverse grooves 136, 137 define a plane perpendicular to the median sagittal plane PSM.

Figure 5:
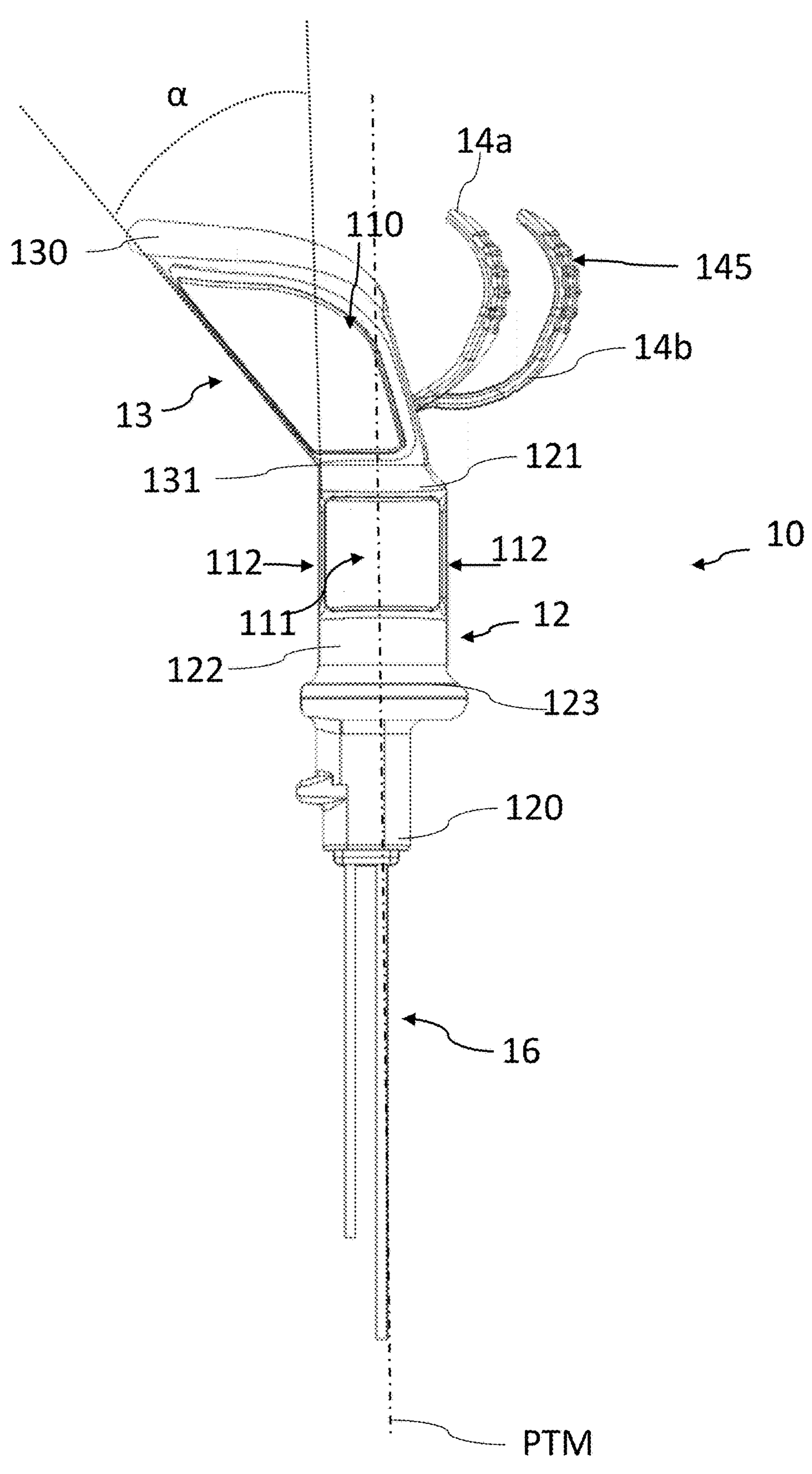
FIG. 5 is a representation as seen from the side of the perineal probe in FIG. 1, two tongues of different size being represented by way of comparison, and the angle of inclination of the flared portion also being represented diagrammatically.

In the FIG. 5 example the flared portion 13 extends at an angle of inclination α relative to a lateral wall 122 of the cylindrical portion 12. Here the angle of inclination α may be between 7° and 40° inclusive. The angle of inclination α may also be between 15° and 30° inclusive. The inclination of the flared portion 13 makes it possible to adapt the conformation of the perineal probe 10 to the natural anterior-posterior inclination of the vagina relative to the pelvic floor. The inclination of the flared portion 13 makes it possible to improve the comfort of the patient and the retention in position of the perineal probe 10. Furthermore, the inclination of the flared portion 13 serves as a polarizer so that the medical practitioner inserts the perineal probe 10 with the correct anterior-posterior orientation.

As depicted in FIGS. 1 to 3, 5 and 7 to 8, the perineal probe 10 includes a retaining member 14*a*, 14*b*. The retaining member 14*a*, 14*b* is configured to bear on the wall of the endocavity in order to improve the retention in position of the perineal probe 10. In this example the retaining member 14*a*, 14*b* is mobile between a deployed position and a folded position. In the deployed position the retaining member 14*a*, 14*b* projects from the body of the perineal probe 10 and bears on a wall of the endocavity of the patient in order to hold the perineal probe 10 in the appropriate position. Conversely, the folded position of the retaining member 14*a*, 14*b* enables insertion of the perineal probe 10 into the endocavity.

As depicted in FIGS. 1 to 3 and 5, the retaining member 14*a*, 14*b* includes a tongue 140 that projects from the flared portion 13 toward a free end 141. Here the tongue 140 projects in the median sagittal plane PSM of the perineal probe 10. The tongue 140 is elastically deformable in the same manner as the flared portion 13. To this end the tongue 140 may be made of the same material as the body of the perineal probe 10.

The tongue 140 is detachably fixed to the cylindrical portion 12 of the perineal probe 10. This enables the use of a plurality of sizes of tongues 140 as a function of the anatomy of the patient. In known manner the depth of a vagina may vary from one woman to another between 7 and 15 cm on average. The medical practitioner can then choose the size of the tongue 140 as a function of the anatomy of the patient.

FIGS. 7 and 8 depict two sizes of tongues 140 for the retaining member 14*a*, 14*b*. FIG. 5 is a schematic representation of the perineal probe 10 which carries two retaining members 14*a*, 14*b* in order to be able to assess the different size of the tongue 140 of each retaining member 14*a*, 14*b*.

As depicted in FIGS. 7 and 8, the tongue 140 may be divided into three segments. At a first end the tongue 140 includes a fixing segment 142. In this example the fixing segment 142 is configured to cooperate with complementary receiving means 15 on the body of the perineal probe 10. The complementary receiving means 15 are disposed on the body of the perineal probe 10 in the plane PSM.

In the example from FIGS. 1 to 3 the complementary receiving means 15 include a slot 150 the opening of which is on the upper face 124 of the cylindrical portion 12. The slot 150 is in the median sagittal plane PSM. Because of this the tongue 140 is able to extend in this same plane and along the same axis of the lateral opening 133 of the endocavity body 13. In this disposition the tongue 140 in the deployed position projects from the flared portion 13 along an anterior-posterior axis situated in the plane PSM. This disposition in the plane PSM also enables the tongue 140 to be folded through the lateral opening 133 into the internal volume of the flared portion 13. The tongue 140 is folded into the internal volume of the flared portion 13 by deforming elastically.

In the example in FIGS. 7 and 8 the fixing segment 142 is straight and of rectangular section in order to cooperate with the slot 150. The dimensions of the fixing segment 142 are complementary to those of the slot 150. The sections of the slot 150 and of the fixing segment 142 may be other shapes such as a circular, hexagonal, triangular, etc. shape.

Alternatively, in the FIG. 6 example the complementary receiving means 15 comprise a notch 151 on the lateral wall 122 of the cylindrical portion 12. The notch 151 lies in the plane PSM. The notch 151 is complementary to the section of the fixing segment 142 in order to retain the holding member 14*a*, 14*b* during use of the perineal probe 10. To this end the notch 151 forms a locking groove in which the fixing segment 142 is inserted and abutted against the bottom of the notch 151. In the FIG. 6 embodiment the perineal probe 10 does not include anterior-posterior electronic members 112.

The complementary receiving means 15 may also take other forms such as clips or any other type of mechanical receiving means enabling removable fixing of the retaining member 14*a*, 14*b*. The detachable character of the retaining member 14*a*, 14*b* advantageously enables sterilization of the perineal probe 10 after use or choice of a tongue 140 appropriate for the anatomy of the patient.

Still with reference to FIGS. 7 and 8, the tongue 140 includes a spacing segment 143. The spacing segment 143 extends the fixing segment 142 in the direction of the end 141. As depicted in FIGS. 1 to 3 and 6, the spacing segment 143 projects from the receiving means 15 so as to space the tongue 140 from the body of the perineal probe 10. The spacing segment 143 is configured to diverge at an angle from the body of the perineal probe 10. In the present example the spacing segment 143 is curved in a concave manner relative to a central axis of the body of the perineal probe. The central axis extends upward in the plane PSM and is perpendicular to the upper face 124 of the cylindrical portion 12.

Referring to FIGS. 7 and 8, the spacing segment 143 has a radius of curvature p that may be larger or smaller depending on the different sizes of the retaining member 14*a*, 14*b*. The retaining member 14*a* in FIG. 8 has a radius of curvature p greater than the radius of curvature p of the retaining member 14*b* in FIG. 7.

The tongue 140 also includes a bearing segment 144. Here the bearing segment 144 extends between the spacing segment 143 and the free end 141 of the tongue 140. The bearing segment 144 is configured to bear on a wall of the endocavity when the perineal probe 10 is introduced into the endocavity. To this end the bearing segment 144 has a striated surface 145. For example, in a female subject the striated surface 145 of the tongue 140 enables better adhesion to the vaginal wall which itself features striations. In fact, the striated surface 145 improves the retention in position of the perineal probe 10 during a diagnostic protocol or a rehabilitation protocol.

The striated surface 145 is more specifically disposed on an oval portion of the bearing segment 144. The oval portion has a surface curvature like the back of a spoon. When the retaining member 14*a*, 14*b* is in the deployed position the surface curvature improves the contact of the striated surface 145 with the vaginal wall. Moreover, when the retaining member 14*a*, 14*b* is in the folded position the oval portion of the bearing segment 144 is disposed in the internal volume of the flared portion 13. In this folded position the oval portion of the bearing segment 144 is complementary to the half-walls 1321, 1322 in the folded position.

The bearing segment 144 and the half-walls 1321, 1322 then form an insertion head the rounded profile of which facilitates the insertion of the perineal probe 10 into the endocavity. Consequently, before insertion of the perineal probe 10 into the endocavity of a patient the medical practitioner causes the retaining member 14*a*, 14*b* to move to the folded position before exerting pressure on each half-wall 1321, 1322 in order to move the flared portion 13 into the folded position. Once the perineal probe 10 has been inserted into the endocavity the elastic properties of the tongue 140 and the curvature of the spacing segment 143 enable the perineal probe 10 to be locked in position by exerting an anterior-posterior elastic force against the wall of the endocavity. This anterior-posterior force makes it possible to prevent the perineal probe 10 being expelled from the endocavity when the patient performs a positional physical exercise with a view to evaluation of the functional status and/or differentiated and dissymmetrical treatment of the deep layers and the surface layers of the perineum.

As depicted in FIGS. 7 and 8, the dimensions of the retaining members 14*a*, 14*b* may be different depending on the height H of the tongue 140 but also depending on the distance d that corresponds to the offset of the free end 141 relative to the fixing segment 142. To be more specific, the radius of curvature p of the spacing segment 143 and the length of the bearing segment 144 may have different dimensions in order to provide a plurality of maintaining members 14*a*, 14*b* of different sizes. In the FIG. 7 example the bearing segment 144 of the retaining member 14*b* is longer than the bearing segment of the retaining member 14*a* in FIG. 8.

As depicted in FIGS. 1 and 3 to 6, the electronic members 110, 111, 112 are disposed on the flared portion 13 and/or on the cylindrical portion 12.

The perineal probe 10 includes power supply cables 16 for the electronic members 110, 111, 112. In this example the cylindrical portion 12 includes at least one longitudinal passage enabling integration of the power supply cables 16 into the cylindrical portion 12 of the perineal probe 10. In particular, said at least one longitudinal passage extends from the free end 120 of the cylindrical portion 12 as far as a point of contact with each electronic member 110, 111, 112. The power supply cables 16 connect each electronic member 110, 111, 112 to an electronic control unit. In particular, the electronic control unit is capable of managing each electric member 110, 111, 112 in a differentiated manner. The electronic control unit may consist of a computer or any other electronic terminal configured to store and to execute a program for management of the electronic members 110, 111, 112 of the perineal probe 10.

The connectors connecting the power supply cables 16 to the electronic members 110, 111, 112 are integrated into the body of the perineal probe 10 in order to guarantee insulation thereof. FIG. 2 shows two pads 160 at the junction between each half wall 1321, 1322 and the upper face 124 of the cylindrical portion 12. These pads 160 form respective chambers in which contacts of the electric cables 16 are connected to contacts of the electronic members 110, 111, 112.

As an alternative to a wired power supply, the perineal probe 10 may include a rechargeable battery feeding the electronic members 110, 111, 112, remote transmission means (for example, etc.) and an electronic control unit for the electronic members 110, 111, 112. The remote transmission means may consist of a near field transmitter/receiver of radio, Bluetooth, Wi-Fi, NFC, RFID, etc. type. Furthermore the electronic control unit may include a clock, a processor and a memory capable of storing and executing data and algorithms such as a diagnostic program and/or a rehabilitation program previously loaded into the memory.

In accordance with one embodiment of the invention the electronic members 110, 111 are disposed two by two on either side of the median sagittal plane PSM. Each electronic member 110, 111 preferably includes a respective EMG electrode. In the present document the abbreviation "EMG" means "electromyographic".

In FIGS. 4 and 5 the electronic members 112 are disposed on the cylindrical portion 12. In particular, the electronic members 112 are disposed two by two, in anterior-posterior fashion, on either side of a median transverse plane PTM of the perineal probe 10. In accordance with this configuration each electronic member 112 includes a force sensor. The median transverse plane PTM present in FIG. 5 defines a longitudinal plane of symmetry in accordance with a transverse orientation of the perineal probe 10.

The perineal probe 10 may include only electronic members 110, 111 equipped with EMG electrodes or only electronic members 112 consisting of respective force sensors. Nevertheless, the perineal probe 10 may also combine all the electronic members 110, 111, 112 (see FIG. 4). In this case the perineal probe 10 may function in two modes: an EMG mode, in which only the electronic members 110, 111 are active, and a force measurement mode in which only the electronic members 112 are active.

As depicted in FIGS. 3, 4 and 6, the flared portion 13 includes two electronic members 110 disposed on respective opposite sides of a plane of symmetry of the perineal probe 10. In this example the two electronic members 110 are disposed on either side of the plane PSM.

As depicted in FIGS. 4 and 5, each electronic member 110 of the flared portion 13 may extend over more than 50% of the surface of the exterior face of each half-wall 1321, 1322. Each electronic member 110 may preferably extend over more than 70% of the surface of the exterior face of each half-wall 1321, 1322. Also for preference, each electronic member 110 may extend over more than 90% of the surface of the exterior face of each half-wall 1321, 1322. When the electronic member 110 includes an EMG electrode the electrode extends over the whole of the surface of the electronic member 110. Now, a large electrode surface enables wider distribution over the anatomy of the patient of the intensity of the electric current, for example in the context of a program of electrostimulation.

In fact, where electrostimulation electrodes are concerned, the standard 60601-2-10 specifies that the current density of an electrode must not exceed a maximum threshold of 2 mA/cm$^2$. Now, to obtain an electro-induced response at least 30 mA must be applied. Increasing the surface area of the electrode as explained above makes it possible to comply with the standard whilst obtaining a satisfactory electro-induced response.

As depicted in FIG. 5, each electronic member 110 has a trapezoidal shape the upper corners of which are rounded. This shape makes it possible to follow the conformation of each half-wall 1321, 1322 and more broadly of the flared portion 13. The surface of each electronic member 110 is consequently curved. Each electronic member 110 extends upward from the base 131 as far as the free upper end 130 of the flared portion 13.

As depicted in FIGS. 3, 4 and 6, the cylindrical portion 13 also includes two electronic members 111 disposed on either side of a plane PSM of the perineal probe 10. To be more specific, the electronic members 111 are disposed in the upper part of the first section of the cylindrical portion 12. Said upper portion is situated in the vicinity of the second end 121 of the cylindrical portion 12.

FIG. 4 depicts schematically a perineal probe 10 in position in a vaginal cavity in a view from the rear of a cross section of the vaginal cavity.

In this representation the half-walls 1321, 1322 and the electronic members 110 are in contact with the wall 200 of the vaginal cavity. Because of this the electronic members 110 are disposed facing muscles of the deep layer of the perineum that surround the vaginal cavity. The muscles of the deep layer of the perineum include in particular the pubovaginal or pubococcygeus muscles but also the puborectalis muscles. These are pairs of muscles that surround the vaginal and rectal cavity. The ileococcygeus and ischiococcygeus muscles form two perineal cupolas that in physiological terms are manifested in muscular pretension and dispose of potential energy for damping the intra-abdominal pressure. Here the ileococcygeus and ischiococcygeus muscles 210 are represented in contact with the vaginal wall 200. The deep layer of the perineum also includes the puborectalis muscles. In fact, when the perineal probe 10 is inserted in the anal cavity the electronic members 110 are positioned facing the ileococcygeus and ischiococcygeus muscles.

As depicted in FIG. 4, when the perineal probe 10 is in position in the vaginal cavity the electronic members 111 of the cylindrical portion 13 are also placed in contact with the vaginal wall 200 in the vicinity of the opening of the vagina. The electronic members 111 are then disposed facing the muscles of the surface layer of the perineum. The surface muscles of the perineum include in particular the bulbospongiosus and ischiocavernosus muscles. These are also pairs of muscles that surround the bottom end of the vagina and the urethra. From a functional point of view the contraction of the bulbospongiosus and ischiocavernosus muscles reinforces the closure of the urethral sphincters. The surface layer of the perineum also includes the external anal sphincter. When the perineal probe 10 is inserted in the anal cavity the electronic members 111 are positioned facing the external anal sphincter.

Referring to FIGS. 4 and 5, the electronic members 112, which consist of force sensors, are disposed on the top part of the cylindrical portion 12. When the perineal probe 10 is inserted into the endocavity the force sensors are positioned at the level of the surface layer of the perineum. It is thus possible to measure the forces exerted along an anterior-posterior axis on the bottom end of the endocavity. For example, it is possible to deduce from these measurements the functional status of the pubovaginal, bulbospongiosus and ischiocavernosus muscles that surround the vagina and the urethra.

For reasons of hygiene, when the force sensors are used, the perineal probe 10 is inserted into a condom-type envelope before being inserted into the endocavity of a patient. Nevertheless, it is recommended in all cases to decontaminate the perineal probe 10 after each use.

The perineal probe 10 preferably includes two electronic members 110 disposed on the flared portion 13 and two electronic members 111 disposed on the cylindrical portion 12 of the body of the perineal probe 10.

In this configuration it is possible to assess via their EMG activity the functional status of and/or to rehabilitate the muscles of the deep and surface layers of the perineum. The perineal probe 10 is configured to interact in a differentiated manner with anatomical structures disposed on either side of the median sagittal plane of the endocavity of the patient.

In the FIG. 4 example the disposition of the electronic members 110, 111 on either side of the mean sagittal plane PSM of the perineal probe 10 enables differentiated treatment of the bundles of iliococcygeus and ischiococcygeus and/or pubovaginal, ischiocavernosus and bulbospongiosus muscles that are situated on either side of the vagina. The perineal probe 10 therefore enables diagnosis and/or treatment of a dissymmetrical functional status of these muscles.

Furthermore, the perineal probe 10 is configured to interact in a differentiated manner with anatomical structures that surround the endocavity of the patient disposed in two distinct anatomical planes. Referring to FIG. 4, the disposition of the electronic members 110, 111 on the cylindrical portion 12 and on the flared portion 13 enables independent treatment of the muscles of the surface and deep layers of the perineum.

The possibility of differentiated treatment of the muscles situated on either side of the vagina in two different anatomic planes is also made possible by the fact that each electronic member 110, 111 includes its own electrical cable 16 that connects it independently to a control unit.

As indicated in the introductory part of the present document, the continence phenomenon is a complex phenomenon that involves a plurality of groups of muscles as much in terms of their tone as in terms of their reactivity as in terms of the quality of the myotatic and conditioned reflexes.

The first group of muscles involved corresponds to the urethra and anal sphincters that respectively surround the urethra and the anal passage. Because of the effect of the respective contraction of these muscles, the urethra and the anal passage are closed.

The muscles of the perineum constitute a second group of muscles that participate in the continence mechanism. The surface layer of muscles of the perineum surrounds the lower end of the urethra, the vagina and the anal passage. Whereas the deep muscles of the perineum form two perineal cupolas that are in muscular pre-tension and have a potential energy for damping the intra-abdominal pressure. The deep muscles also surround the vaginal cavity in a deeper anatomical layer.

As has been indicated, the deep and surface muscles of the perineum do not have the same role in the continence mechanism. The deep muscles of the perineum have a function of damping the increased intra-abdominal pressure, which is a phenomenon triggering a potential situation of urinary or fecal leakage. The surface muscles of the perineum for their part participate in closing the urethra or the anal passage.

During a clinical examination the perineal probe 10 is inserted into the endocavity of a patient before the latter performs exercises that usually lead to urinary or fecal leakage: coughing, bending the knee, leaning forward, carrying loads, etc.

During these exercises the perineal probe 10 enables measurement via the EMG activity of the tone of the surface and deep muscles of the perineum, the perineal anticipation reflex, the muscle tone after the perineal reflex, the myotatic reflex, and also the response of the rapid muscular fibers initiated by this reflex.

Furthermore, by tracking the forces that are applied to the force sensors via the wall of the endocavity it is also possible to assess the tone of the deep and surface layers of the perineum, the perineal anticipation reflex, the response of the rapid fibers, the timing of the myotatic reflex (is it present? or delayed?), etc.

Figure 9:
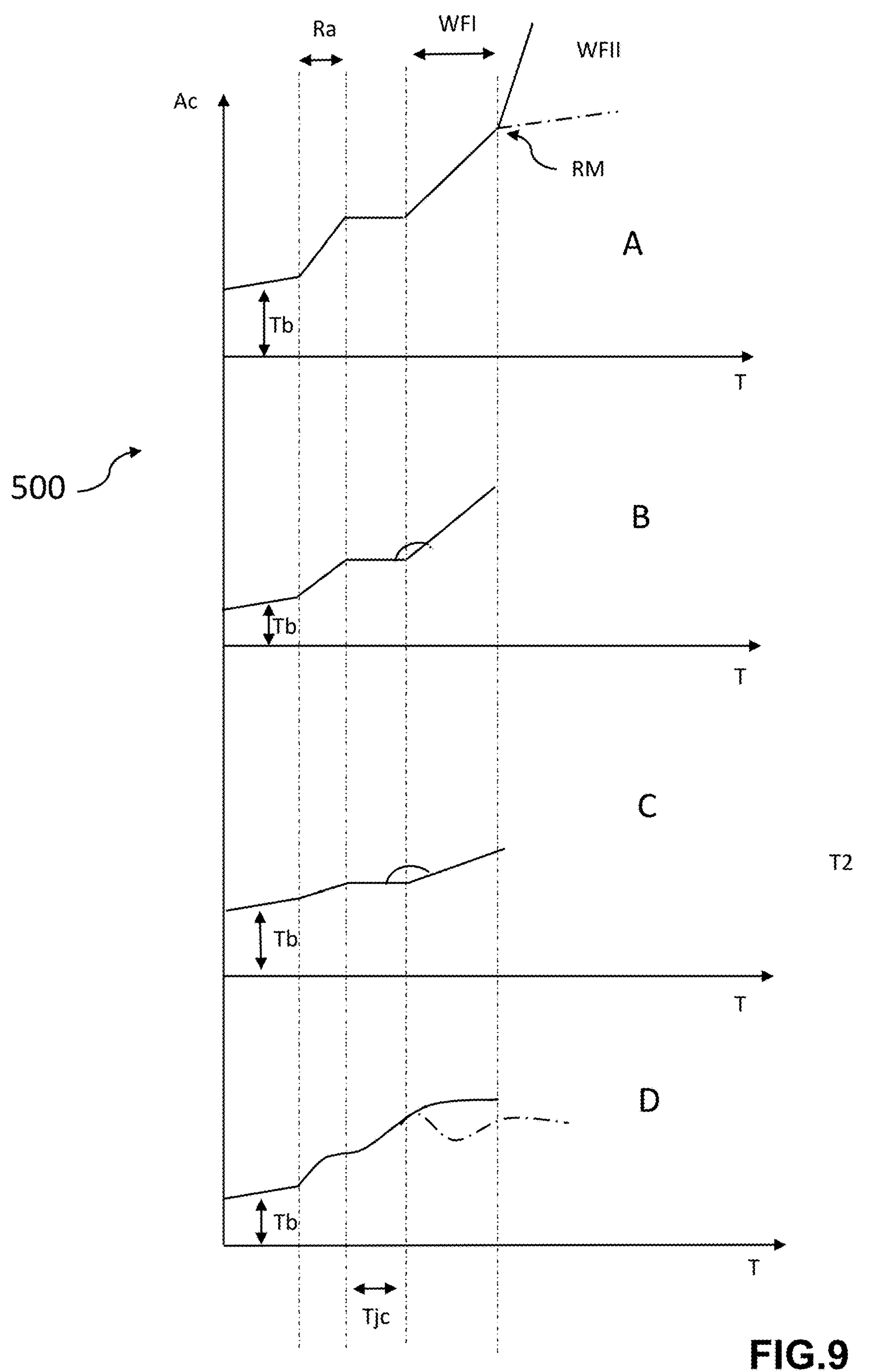
FIG. 9 is a schematic graph representing data on neuromuscular activity that can be measured with the aid of the electronic members of a perineal probe in accordance with the invention.

The graph 500 in FIG. 9 depicts schematically four traces A, B, C, D as a function of time T of the neuromuscular activity Ac measured by the electronic members 110, 111, 112 of the perineal probe 10 in accordance with the invention.

The trace A corresponds to data measured by a posterior force sensor of the electronic member 112. The latter is placed at the level of the surface layer of the perineum. Firstly, there is measured the basic tone Tb of the endocavity and the surface muscles of the perineum. When the patient prepares to perform a movement leading to an increase in the intra-abdominal pressure, there is seen in the graph 500 an increase in the neuromuscular activity that corresponds to the perineal anticipation reflex Ra that activates the fibers I. The data measured after the anticipation reflex Ra corresponds to the tone of the connecting tissue Tjc as increased by the increased neuromuscular activity (fiber I). In theory, the tone of the functional connecting tissue is seen as a trace in the form of a plateau as in the trace A depicted.

In response to the muscular stretching generated by the increased intra-abdominal pressure, the recruitment of the muscular fibers of type I or slow fibers progressively increases the muscular contraction and the closing pressure (urethra and anal). This phase is denoted WFI in trace A. When the stretching reaches a particular threshold, the myotatic reflex RM triggers the response WFII of the muscular fibers of type II or rapid fibers. The trace A includes a continuous line the slope of the curvature of which increases significantly after the myotatic reflex RM and a curve in chain-dotted line for which the slope of the curve decreases. Now, the chain-dotted section of the curve of trace A is characteristic of a dysfunction of the rapid fibers or of the myotatic reflex.

The traces B and C in the graph 500 correspond to the data measured by the EMG sensors of the respective electronic members 110 of the flared portion 13. These traces therefore correspond to the activity of the perineal muscles on either side of the plane PSM. Note on trace C a hypertonicity of the basic tone Tb and a profile of less marked curvature than that of trace B. Such traces can reveal a functional dissymmetry of the perineal cupolas. This dissymmetry may be encountered in a pregnant woman, depending on the position of the head of the baby. Nevertheless, dissymmetric hypertonicity can also be caused by an obstetric, physical or psychological trauma.

The trace D in diagram 500 corresponds to the data measured by the anterior force sensor of the electronic member 112. The latter is placed at the level of the surface layer of the perineum. In this trace the chain-dotted trace corresponds to degraded quality of the connecting tissue of the perineum.

The perineal probe 10 enables differentiated diagnoses of the various muscles that constitute the surface and deep layers of the perineum to be established. In particular, differentiated evaluation is possible of the functional status of the two pairs of bundles of ileococcygeus and ischiococcygeus and/or pubovaginal and puborectalis muscles (deep layers), bulbospongiosus muscles and ischiocavemosus muscles (surface layers).

The perineal probe 10 enables precise dysfunctioning to be established: hypertonicity or hypotonicity of the basic tone and/or of the tone of the connecting tissue, dysfunction of the rapid fibers and/or the slow fibers, absence or delayed anticipation reflex, absent or delayed myotatic reflex, etc. The measured data may be interpreted directly or by comparison with a reference database.

Once the diagnosis has been established, the perineal probe 10 enables recommendation of a functional rehabilitation protocol that can be targeted on the anatomical structures that have a disturbed functional status. Depending on the problem identified, the medical practitioner can apply via the EMG electrodes electrostimulation programs adapted to treat the dysfunction or dysfunctions that have been diagnosed.

The invention claimed is:

1. Perineal probe comprising, a probe body which includes a cylindrical portion configured to be positioned at an opening of a vaginal or anal endocavity of a patient, a flared portion which extends from one end of the cylindrical portion, the flared portion extends at an inclined angle relative to the cylindrical portion to a free upper end, the flared portion being elastically deformable between a folded position and a deployed position so as to rest on the walls of the vaginal or anal endocavity, and electrodes configured to interact with muscles of the perineum of the patient, the electrodes being disposed on the flared portion and/or on the cylindrical portion, wherein the flared portion includes a lateral wall comprising an exterior surface and an inner surface opposite to the exterior surface, the inner surface of the lateral wall defines a conical internal volume and comprises a longitudinal groove extending along a plane of symmetry of the perineal probe such that the longitudinal groove divides the lateral wall into two half walls.

2. The perineal probe as claimed in claim 1, wherein the flared portion includes two additional grooves that extends transversely relative to the plane of symmetry of the perineal probe, the two additional grooves extend on the exterior surface of the lateral wall at a base of the flared portion disposed at the junction between the flared portion and the cylindrical portion.

3. The perineal probe as claimed in claim 1, in which the flared portion includes at least one opening disposed in the plane of symmetry of the perineal probe.

4. The perineal probe as claimed in claim 3 in which the at least one opening along the flared portion includes:

a lateral opening disposed in a plane of symmetry of the perineal probe, and a top opening disposed at the level of the free upper end of the flared portion.

5. The perineal probe as claimed in claim 1, including a retaining member which projects from the flared portion and is mobile between a deployed position and a folded position, in which, in the deployed position, the retaining member enables the flared portion is adapted to be retained in position in the vaginal or anal endocavity of the patient and, in the folded position, the retaining member enables insertion of the perineal probe into the vaginal or anal endocavity.

6. The perineal probe as claimed in claim 5, in which the retaining member includes a tongue that projects from the flared portion and comprises a free end such that the tongue projects along the plane of symmetry of the perineal probe.

7. The perineal probe as claimed in claim 6, in which the tongue has a striated surface at its free end.

8. The perineal probe as claimed in claim 5, in which the retaining member is attached to the cylindrical portion in a detachable manner.

9. The perineal probe as claimed in claim 6, in which in the deployed position the tongue projects from the flared portion from the plane of symmetry in an anterior-posterior direction.

10. The perineal probe as claimed in claim 1, in which the flared portion extends at the inclined angle relative to a lateral wall of the cylindrical portion, the inclined angle is between 7° and 40° inclusive.

11. The perineal probe as claimed in claim 1, in which the flared portion comprises two electronic members disposed on either side of the plane of symmetry of the perineal probe.

12. The perineal probe as claimed in claim 1, in which the cylindrical portion includes electronic members disposed on either side of the plane of symmetry of the perineal probe.

13. The perineal probe as claimed in claim 9, in which the cylindrical portion and the flared portion include respective electronic members consisting of EMG electrodes, the electronic members being disposed on either side of a plane transverse to the plane of symmetry of the perineal probe.

14. The perineal probe as claimed in claim 12, in which the electronic members disposed in an anterior-posterior direction on either side of a plane transverse of the plane of symmetry of the perineal probe include two force sensors.

* * * * *